United States Patent
Hang et al.

(10) Patent No.: US 10,538,549 B2
(45) Date of Patent: Jan. 21, 2020

(54) NNA-DNA ADDUCTS AS BIOMARKERS FOR DETECTING EXPOSURE TO THIRDHAND SMOKE

(71) Applicants: Bo Hang, Lafayette, CA (US); Ahmed Chenna, Sunnyvale, CA (US)

(72) Inventors: Bo Hang, Lafayette, CA (US); Ahmed Chenna, Sunnyvale, CA (US)

(73) Assignee: The Regents of the University of California, Oakland, CA (US)

( * ) Notice: Subject to any disclaimer, the term of this patent is extended or adjusted under 35 U.S.C. 154(b) by 859 days.

(21) Appl. No.: 14/659,588

(22) Filed: Mar. 16, 2015

(65) Prior Publication Data

US 2016/0039859 A1    Feb. 11, 2016

Related U.S. Application Data

(60) Provisional application No. 61/953,842, filed on Mar. 16, 2014, provisional application No. 61/953,844, filed on Mar. 16, 2014.

(51) Int. Cl.
*G01N 33/53* (2006.01)
*C07H 19/23* (2006.01)
*C07H 19/16* (2006.01)

(52) U.S. Cl.
CPC ............ *C07H 19/16* (2013.01); *C07H 19/23* (2013.01); *G01N 33/5308* (2013.01)

(58) Field of Classification Search
CPC ..... C07H 19/16; C07H 19/23; G01N 33/5308
See application file for complete search history.

(56) References Cited

U.S. PATENT DOCUMENTS

2005/0043515 A1 * 2/2005 Brown ................... C07K 16/16
530/387.1

OTHER PUBLICATIONS

Sleiman et al. Formation of carcinogens indoors by surface-mediated reactions of nicotine with nitrous acid, leading to potential thirdhand smoke hazards. PNAS 2010, vol. 107, No. 15, pp. 6576-6581. (Year: 2010).*
Hang et al. Thirdhand smoke causes DNA damage in human cells. Mutagenesis 2013, vol. 28, No. 4., pp. 381-391. (Year: 2013).*
Mesoros et al. 8-oxo-2'-deoxyguanosine as a biomarker of tobaco smoking induced oxidative stress. Free Radic Biol. Med. 2012, vol. 53, No. 3, pp. 610-617. (Year: 2012).*
Herrero et al. 8-oxo-deoxyguanosine levels in heart and brain mitochondrial and nuclear DNA of two mammals and three birds in relation to their different rates of aging. Aging Clin. Exp. Res. 1999, vol. 11, pp. 294-300. (Year: 1999).*

* cited by examiner

*Primary Examiner* — Shafiqul Haq
(74) *Attorney, Agent, or Firm* — Michelle Chew Wong; Lawrence Berkeley National Laboratories

(57) ABSTRACT

NNA-derived specific adducts represent an integrated biomarker of exposure to thirdhand smoke (THS) as NNA is unique to THS. The NNA-dG covalent binding adduct could serve as such a biomarker, and play a role in identifying individuals exposed to THS, thus providing critical information for early detection and prevention.

13 Claims, 13 Drawing Sheets

FIG. 1: NNA is uniquely found in thirdhand smoke (THS)

Acute and THS+HONO | Chronic

Hang et al. Mutagenesis 2013

In the comet assay, NNA caused concentration-dependent DNA strand breaks at non-cytotoxic concentrations for 24 hrs (A). NNK, a known carcinogen, was used as a positive control (B).

In the comet assay, NNA caused concentration-dependent DNA strand breaks at non-cytotoxic concentrations for 24 hrs (A). NNK, a known carcinogen, was used as a positive control (B).

FIG: 5

- Molecular formula: $C_{20}H_{22}N_8O_5$ or $C_{20}H_{23}N_8O_5^+$
- Molecular weight: 454.18 (M) or 455.18 (M+H)$^+$
- Addition of neutral $C_{10}H_9N_3O$ to dG
- Addition of NNA minus 4 hydrogens and 1 oxygen The m/z 455.18 is a condensation product of NNA and dG with the elimination of $H_2O$ and H2 molecules.

FIG. 8: Other Newly identified NNA-induced dG lesions

FIG. 9
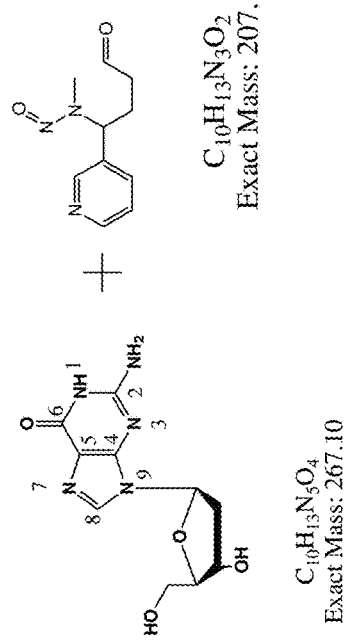
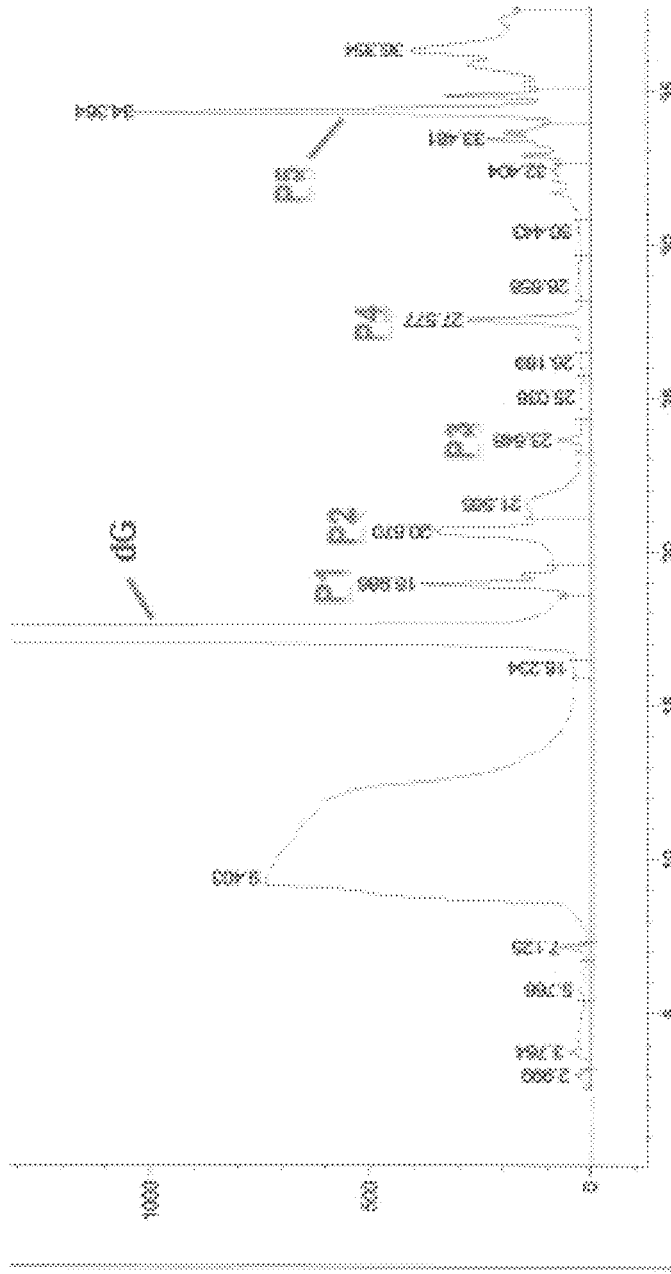
NNA forms both base and sugar adducts *in vitro*

NNA-DNA ADDUCTS AS BIOMARKERS FOR DETECTING EXPOSURE TO THIRDHAND SMOKE

CROSS-REFERENCE TO RELATED APPLICATIONS

This application is a non-provisional of and claims priority to U.S. Provisional Patent Application Nos. 61/953,842 and 61/953,844, both filed on Mar. 16, 2014, and both hereby incorporated by reference in their entireties.

STATEMENT OF GOVERNMENTAL SUPPORT

This invention was made during work supported by U.S. Department of Energy under Contract No. DE-AC02-05CH11231 and by Grant Nos. 19XT-0070 and 19ST-0185 awarded by the Tobacco-Related Disease Research Program (TRDRP) of the State of California. The government has certain rights in this invention.

BACKGROUND OF THE INVENTION

Field of the Invention

The present invention relates to NNA-DNA adducts as biomarkers and methods and compositions for monitoring and detecting these NNA-DNA adducts.

Related Art

A major challenge in biomonitoring and prevention of thirdhand smoke is the identification of unique biomarkers from the biological response to thirdhand smoke (THS) exposure, particularly of those from nicotine, the major compound found in thirdhand smoke. There has previously been no success in identification of unique or specific biomarkers (such as toxican metabolites and reaction products) for assessing thirdhand smoke exposure. This is a novel field and market and no similar products or markers for detection exist.

BRIEF SUMMARY OF THE INVENTION

Thirdhand smoke (THS) exposure is a potential new health risk as recent indoor chemistry studies have revealed that sorbed nicotine reacts with the common indoor pollutant nitrous acid (HONO) to form mutagenic tobacco-specific nitrosamines (TSNAs). Bulky DNA adducts are formed by the covalent binding of chemical carcinogens to various sites on DNA bases, representing a major and important class of DNA damage originating from exposure to cigarette smoke. These adducts represent an integrated biomarker of exposure to specific chemical compounds in cigarette smoke.

1-(N-methyl-N-nitrosamino)-1-(3-pyridinyl)-4-butanal (NNA) is the major TSNA product identified herein from THS, and is absent in freshly emitted secondhand smoke. Given that NNA is only found in THS, its derived covalent bulky adduct would serve as a specific biomarker of THS exposure. It is also a challenge to identify and characterize the structures of bulky adducts resulting from covalent binding of NNA to DNA, however, herein we describe the structure of these adducts.

We recently examined the genotoxicity of NNA in human HepG2 cells as well as its ability to modify both 2-deoxyguanosine (dGuo) and 2-deoxycytodine (dCyt) in vitro. In alkaline comet assay, it caused concentration-dependent DNA strand breaks in HepG2 cells at non-cytotoxic concentrations ranging from 0.01 mM to 100 mM for 24 hours. In the reaction of NNA with dGuo, several adducts were identified with HPLC-UV spectrum, ESI-MS/MS and NMR. These include 8-oxo-2'-deoxyguanosine (8-oxo-dG), $O^6$-methyl-dG, and $N^2$-methyl-dG. NNA also forms a bulky dG adduct with m/z 455.17 for $(M+H)^+$ in mass spectrum, which is due to the condensation of NNA and dG with the elimination of $H_2O$ and two hydrogen molecules. In addition, NNA causes novel DNA sugar damage, forming 5' & 3'-methyl-dG. Taken together, these results provide evidence for the DNA damaging potential of NNA, which, in part, may contribute to THS-induced adverse health effects in humans. In addition, the NNA-specific DNA adducts identified can be used as specific biomarkers of THS exposure.

Thus the present invention provides for methods and compositions for the detection of the presence of DNA damage in a cell as a result of exposure to thirdhand smoke. Herein is also described methods for monitoring and detecting the presently described NNA-specific DNA markers. Further work in validating them in human lab and field studies is also contemplated.

In one embodiment, a specific antibody to detect the NNA-DNA adduct is made, thereby providing methods and compositions for an immunoassay platform test kit that can be used for THS exposure-related environmental health monitoring in human subjects. Human blood will be taken and used for detection, and such a test will be simple, inexpensive, and NNA (thus THS)-specific. Methods of detection may involve using existing technology such as mass spectrometry and imaging, e.g., LC-Mass Spec.

In another embodiment, the use of NNA-DNA adduct-based test kits/devices among people with potential THS exposure or any person with signs and symptoms that are suspected to be associated with exposure to THS.

BRIEF DESCRIPTION OF THE DRAWINGS

FIG. 9: NNA forms both base and sugar adducts in vitro

DETAILED DESCRIPTION OF THE PREFERRED EMBODIMENT

Figure 1:
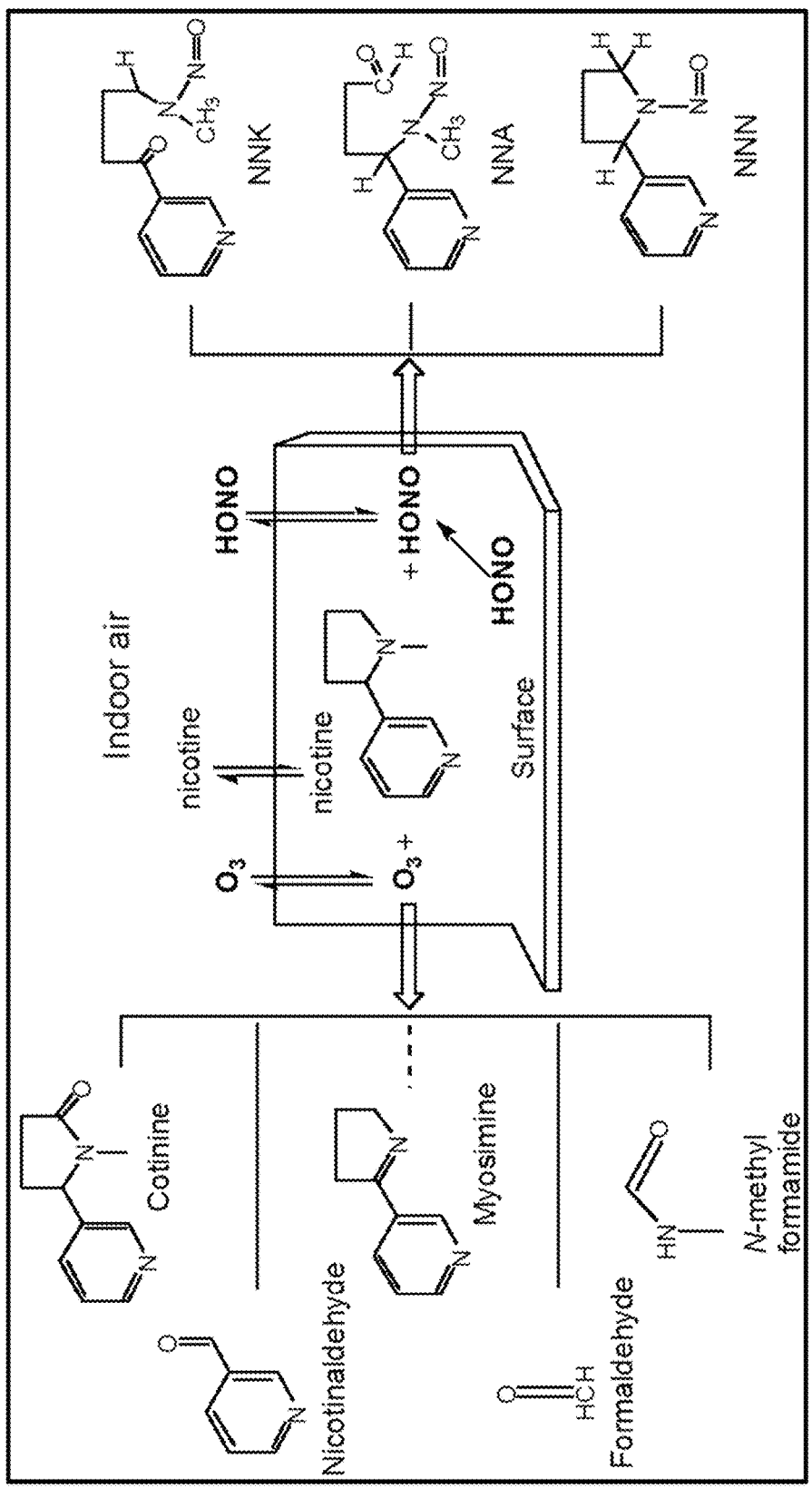
FIG. 1: NNA is uniquely found in thirdhand smoke (THS)
Figure 2:
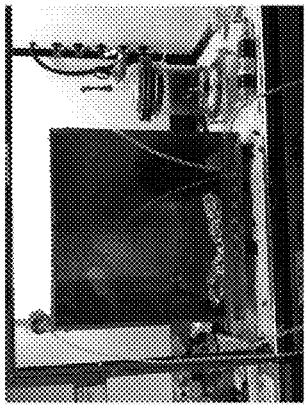
FIG. 2: NNA is identified in both acute and chronic THS samples generated from lab systems

NNA (1-(N-methyl-N-nitrosamino)-1-(3-pyridinyl)-4-butanal) is an important member of the carcinogenic/mutagenic tobacco-specific nitrosamines (TSNAs) and an unique constituent found in the most recently identified health risk called thirdhand smoke (THS). We studied the reactions of NNA with 2-deoxyguanosine (dGuo) and 2-deoxycytidine (dCyt) in vitro with regard to its ability to form stable base adducts, which have not been reported in literature at all. Herein we have identified and characterize potential specific THS biomarkers. We also describe experimental evidence for detrimental effects from exposure to THS, which could be useful for framing and enforcing new policies against indoor smoking.

We discovered that NNA reacts with dGuo ("dG") and dCyt ("dC") to form various DNA adducts. NNA forms a novel covalent adduct with the base of dGuo, which exhibits a characteristic UV spectrum with λmax270 nm and 285 nm, and λmin250 nm. Electrospray ionization mass spectrometry (ES-MS/MS) showed a m/z 455.17 for (M+H)+ in mass spectrum, which is due to the condensation of NNA and dGuo with the elimination of $H_2O$ and two hydrogen molecules (addition of neutral $C_{10}H_9N_3O$ to dGuo). The chemical structure of this adduct has been proposed and validated using various NMR experiments. Because of its specific structural characteristic, this adduct can serve as a DNA damage "signature" by NNA, thus a potential biomarker for monitoring exposure to thirdhand smoke.

From the NNA and dGuo ("dG") reactions, we also found, for the first time, two methylated dGuo adducts, O6- and N2-methyl-dGuo, 7,8-dihydro-8-oxo-deoxyguanosine (8-oxo-dGuo), and a novel DNA sugar damage, 5' & 3'-methyl-dGuo.

In some embodiments, multiple products are detected and identified structurally from the reaction of NNA with dG in vitro, including 8-oxo-dG, $N^2$-methyl-dG, $O^6$-methyl-dG, 5',3'-Methyl-dG (sugar damage) and a specific covalent bulky adduct with m/z 455.18. The structures of select NNA products are shown below:

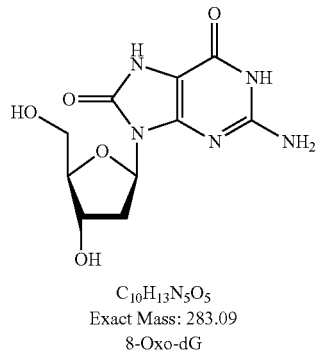

$C_{10}H_{13}N_5O_5$
Exact Mass: 283.09
8-Oxo-dG

-continued

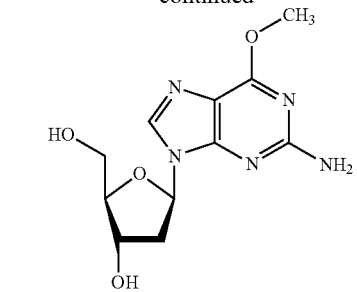

$C_{11}H_{15}N_5O_4$
Exact Mass: 281.11
$O^6$-methyl-dG

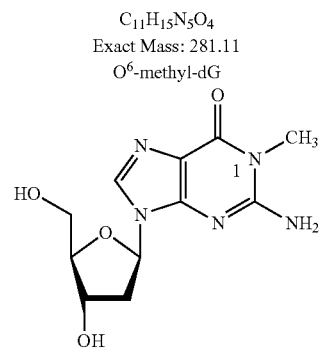

$C_{11}H_{15}N_5O_4$
Exact Mass: 281.11
$N^2$-methyl-dG

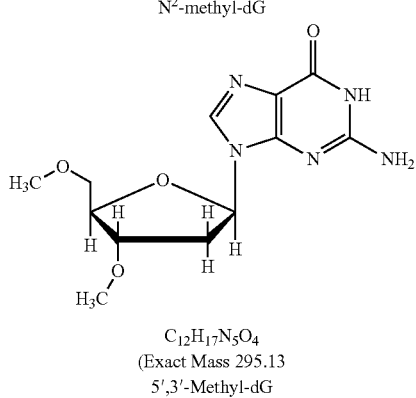

$C_{12}H_{17}N_5O_4$
(Exact Mass 295.13
5',3'-Methyl-dG

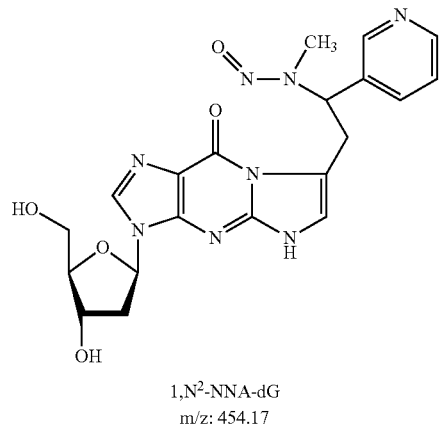 [SMILES: CN(N=O)C(Cc1c[nH]c2nc3c(ncn3[C@H]3C[C@@H](O)[C@@H](CO)O3)c(=O)n12)c1cccnc1]

1,$N^2$-NNA-dG
m/z: 454.17

Herein we describe the first evidence that reaction of NNA with dCyt in vitro results in formation of stable base adducts too, which have not been hereto for been reported in literature.

In some embodiments, methods of detection of NNA and/or dG adducts are provided. The detection of these NNA and/or dG adducts can be carried out using any means of detection currently known. For example, detection can be by mass spectrometry, spectroscopy, nuclear magnetic resonance, oxidation—reduction reactions such as $NaBH_4$ reduction, thermal hydrolysis, positron emission tomography, fluorescence or other labeled detection, immunohistochemistry, or other imaging technique. In some embodiments, NNA and/or the dG adducts are detected by fluorescence or labeled antibody, small molecule, compound, or probes.

In one embodiment, the sample UV spectra is compared to the spectral peaks observed from ESI-MS, and NMR to determine the mass of the NNA or dG adduct detected.

In one embodiment, an antibody is generated for the specific NNA or DNA adduct to be detected. Polyclonal and monoclonal antibodies can be made by well-known methods in the art. In one embodiment, a method of generating these antibodies is by first synthesizing the adduct and conjugated to a carrier protein before use such as, Keyhole limpet hemacyanin (KLH). The conjugated adduct can then be mixed with adjuvant and injected into a mammal, preferably a rabbit through intradermal injection, to elicit an immunogenic response. Samples of serum can be collected and tested by ELISA assay to determine the titer of the antibodies and then harvested. Polyclonal (e.g., anti-8-oxo-dG) antibodies can be purified by passing the harvested antibodies through an affinity column. Monoclonal antibodies are preferred over polyclonal antibodies and can be generated according to standard methods known in the art of creating an immortal cell line which expresses the antibody.

In some embodiments, a sample from a subject is obtained. The sample may be a fluid or tissue sample. A fluid sample can be a blood, saliva, urine, fecal, aspirate or other bodily fluid sample. The tissue can be from any bodily tissue. In some embodiments, it may be preferred from tissues that are exposed to thirdhand smoke such as the skin, nasal, lung, liver or other tissue.

The sample can be analyzed and undergo analysis to determine the presence or level of the NNA adduct in the sample. In some embodiments, a method for detection of sample exposure to thirdhand smoke is present in a sample, comprising the steps of (a) providing a detector which detects the presence of a dG adduct and/or NNA in a sample, and (b) initiating a notification signal to indicate the presence of a dG adduct and/or NNA, wherein the detection of NNA or any of its dG adducts indicates prior exposure to thirdhand smoke.

In another embodiment, methods and compositions for the detection of the presence of DNA damage in a cell as a result of exposure to thirdhand smoke are also provided. In some embodiments, if the NNA or dG or dC adduct is detected, an assay to evaluate DNA strand breaks is used to determine the level of DNA damage that the subject has encountered due to thirdhand smoke. For example, a comet assay (e.g., single cell gel electrophoresis assay) can be performed. In some embodiments, methods to carry out DNA damage can use specific NNA or dG adduct or dC adduct—specific probes or compositions to specifically detect the THS biomarkers at the chromosomal location of the DNA break.

Example 1

Preparation of Starting Materials

THS exposure is a potential new health risk as recent studies have revealed that sorbed nicotine reacts with the common indoor pollutant nitrous acid (HONO) to form mutagenic tobacco-specific nitrosamines (TSNAs). 1-(N-methyl-N-nitrosamino)-1-(3-pyridinyl)-4-butanal (NNA) is the major TSNA product identified from THS and is absent in freshly emitted secondhand (SHS) tobacco smoke. So far little is known about the genotoxicity of NNA and its DNA adduct forming ability has not been reported.

Figure 3A:
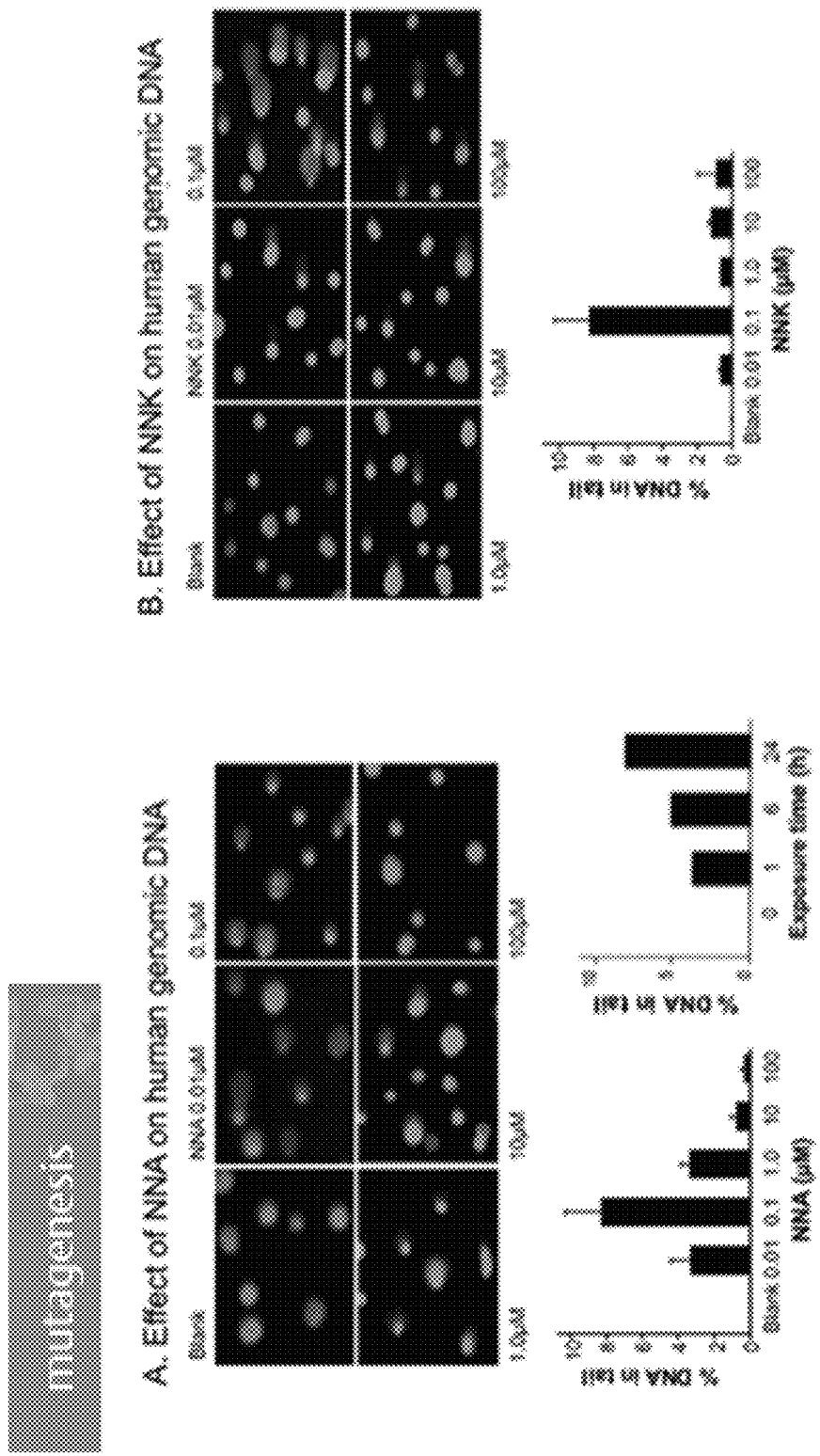
FIGS. 3A and 3B: Genotoxic effect of NNA in human HepG2 cells as measured by the Comet assay. HepG2 cells were exposed to varying doses of NNA dissolved in DMEM medium with/without 10% FBS for 24 h. NNK was used as a positive control as previous studies have showed that the comet assay is sufficiently sensitive and specific in measuring NNK-induced DNA damage, including strand breaks and alkali-labile sites [6]. This study shows that NNA, similar to NNK, induces DNA damage at low nanomolar concentrations. (A) Effect of acute THS and THS+HONO. HepG2 cells were exposed to samples at 37° C. for 24 h. The extent of DNA damage was analyzed by % DNA in tail to total DNA from 90 cells. (B) HepG2 cells were exposed to chronic THS at varying dilutions under identical conditions as above.
Figure 3B:
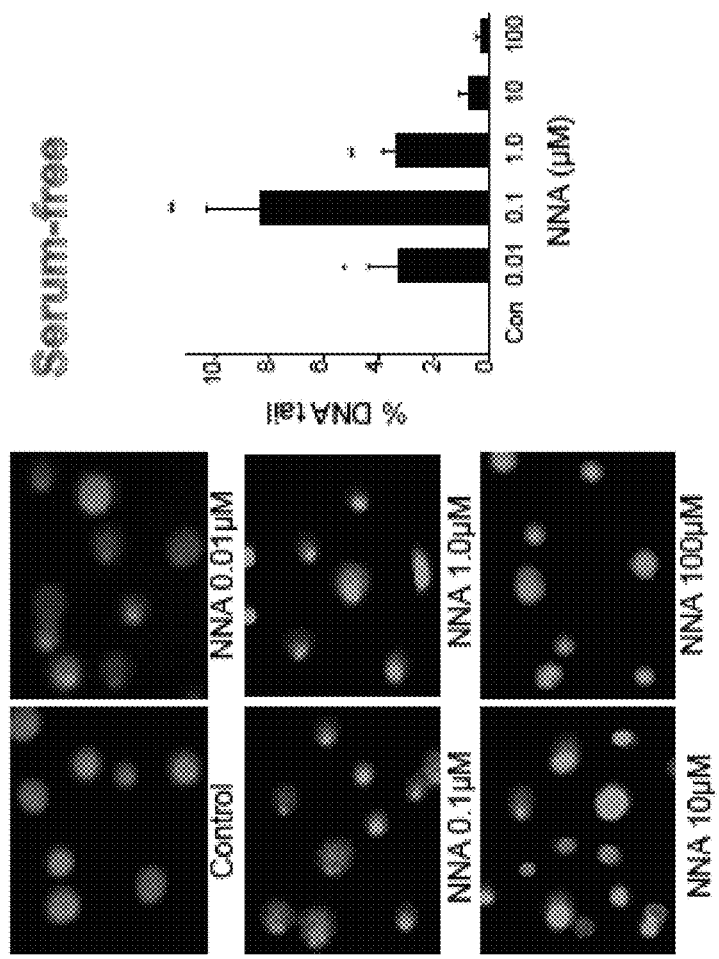
Figure 4:
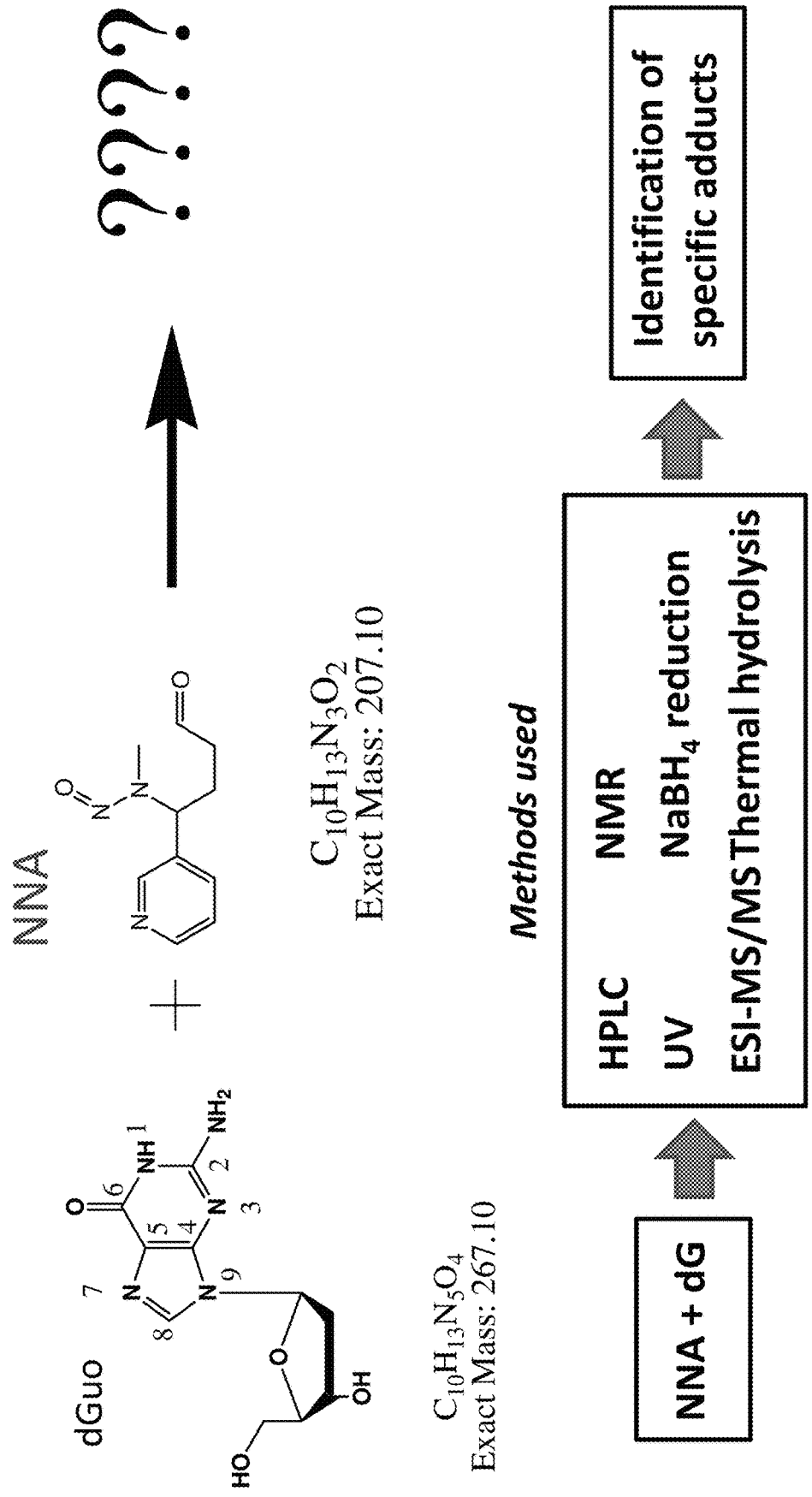
FIG. 4: Reaction of NNA with dG—studies on formation of DNA adducts
Figure 5:
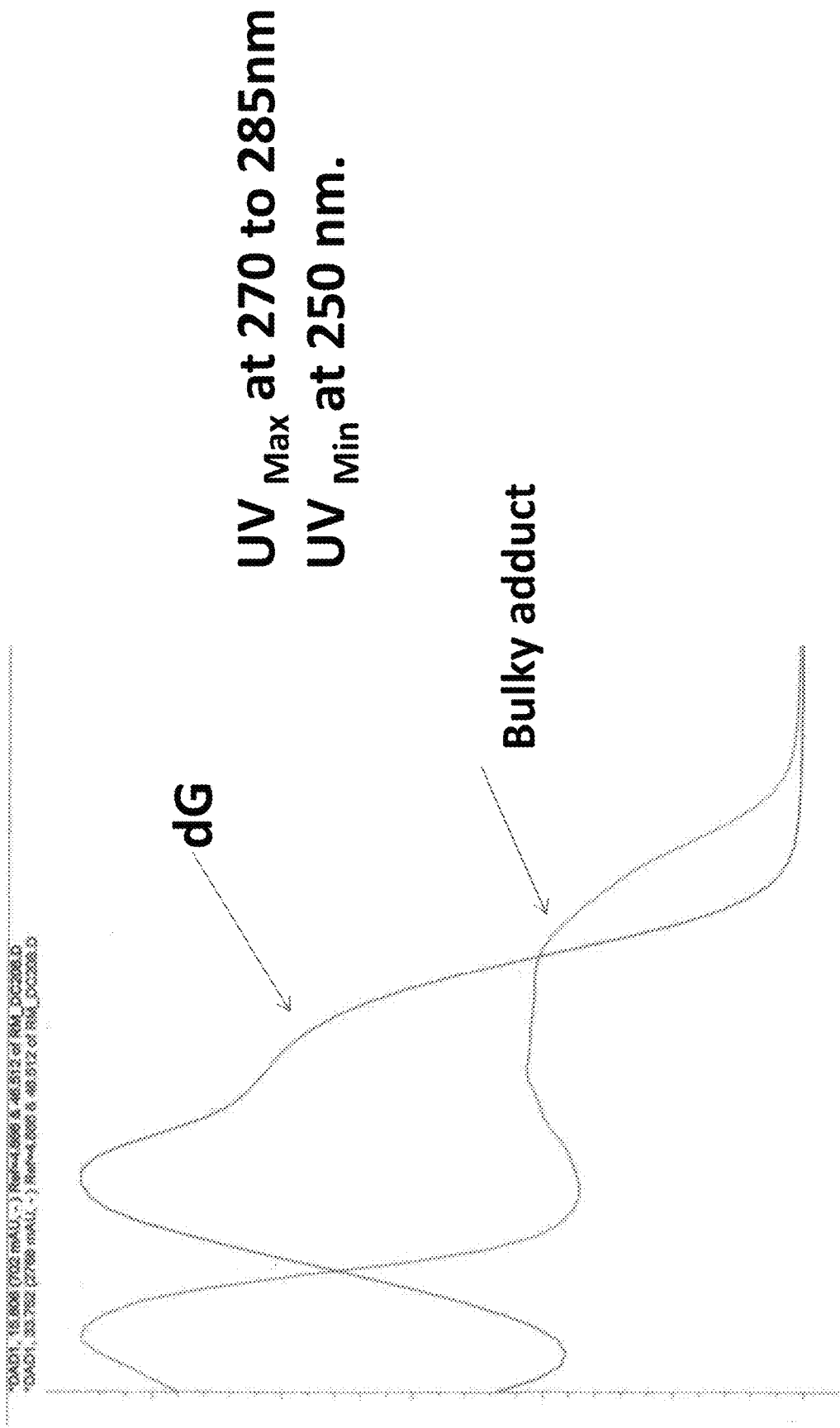
FIG. 5: NNA forms a bulky adduct with dGuo which exhibits a characteristic UV spectrum
Figure 6:
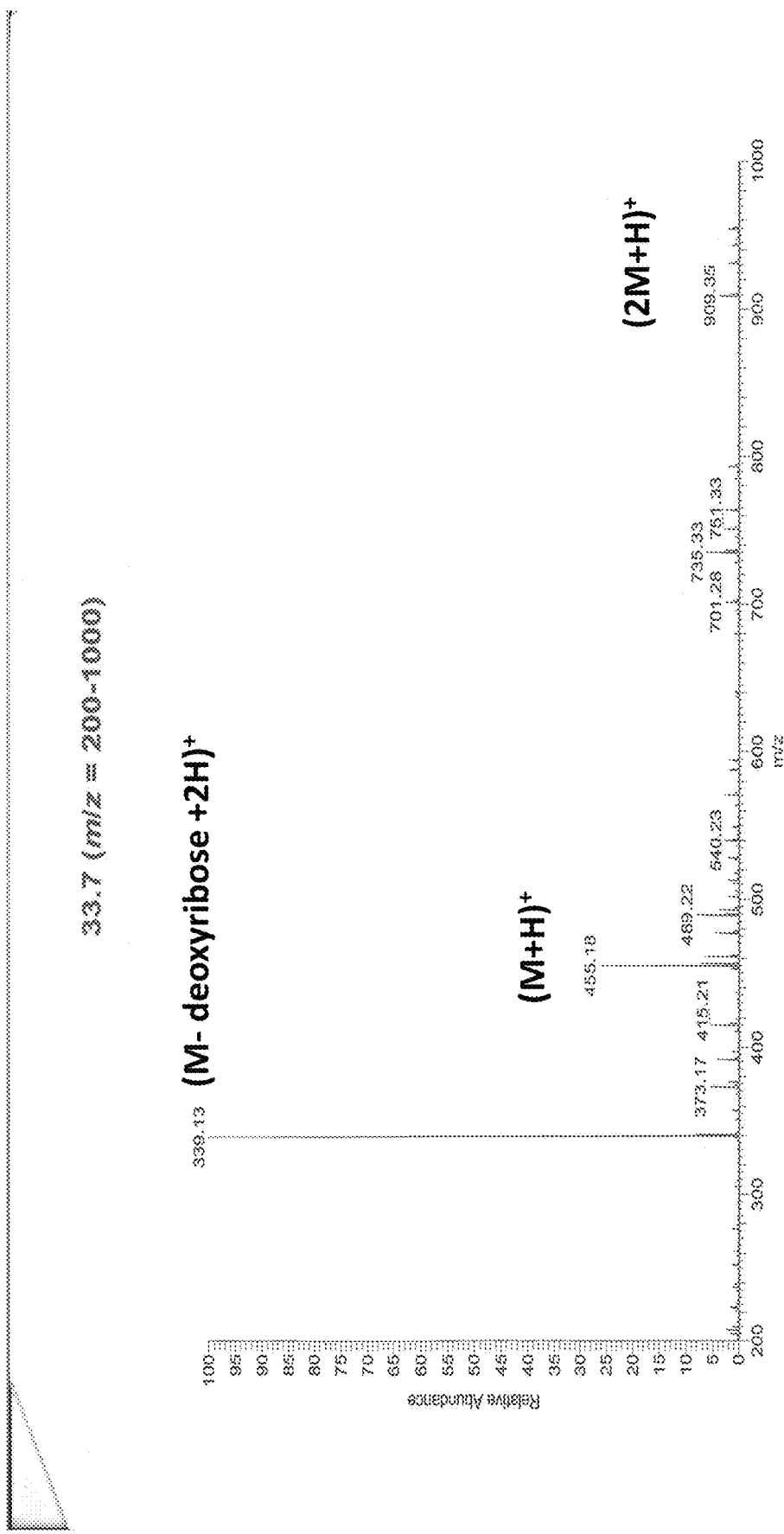
FIG. 6: ESI-MS/MS of the bulky adduct
Figure 7:
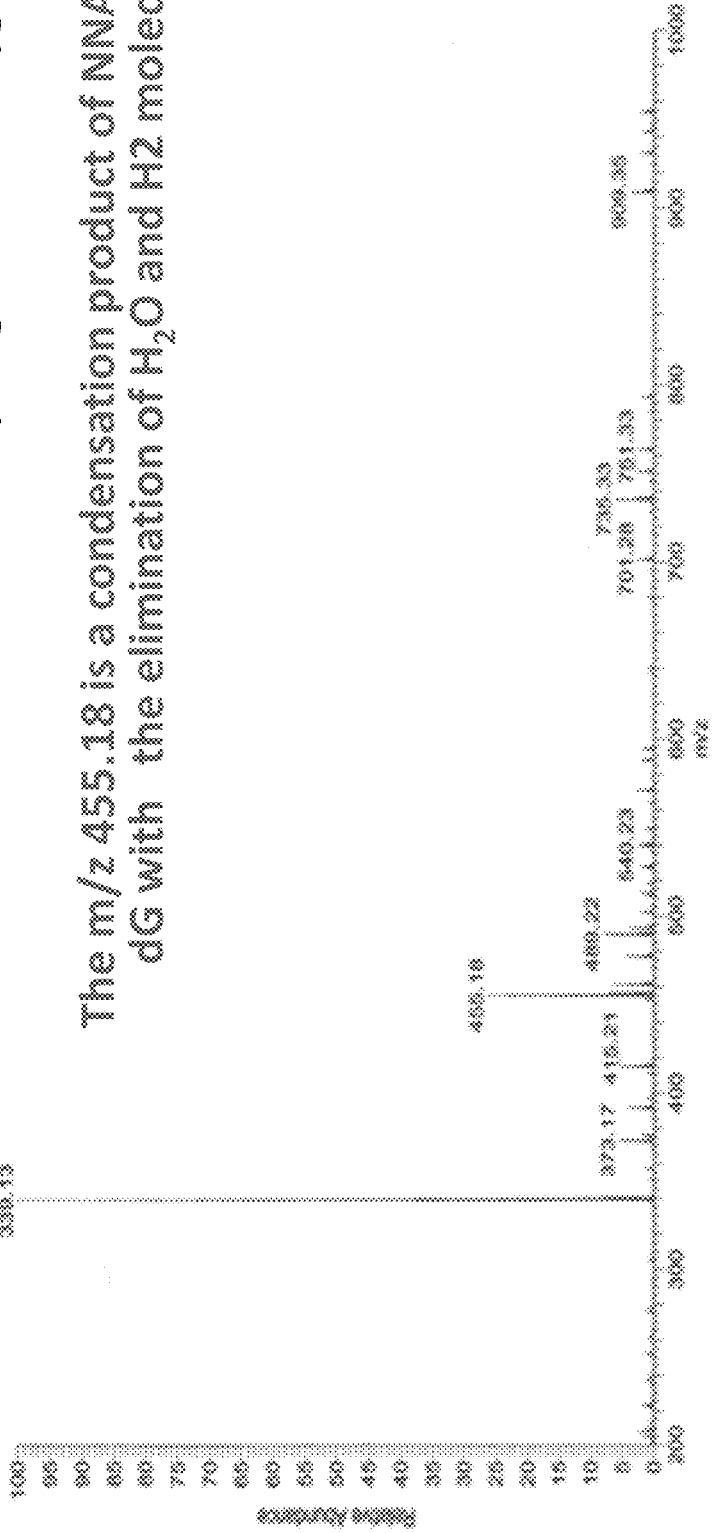
FIG. 7: The newly identified bulky NNA-dG adduct: Summary of the ESI-MS/MS findings.
Figure 8:
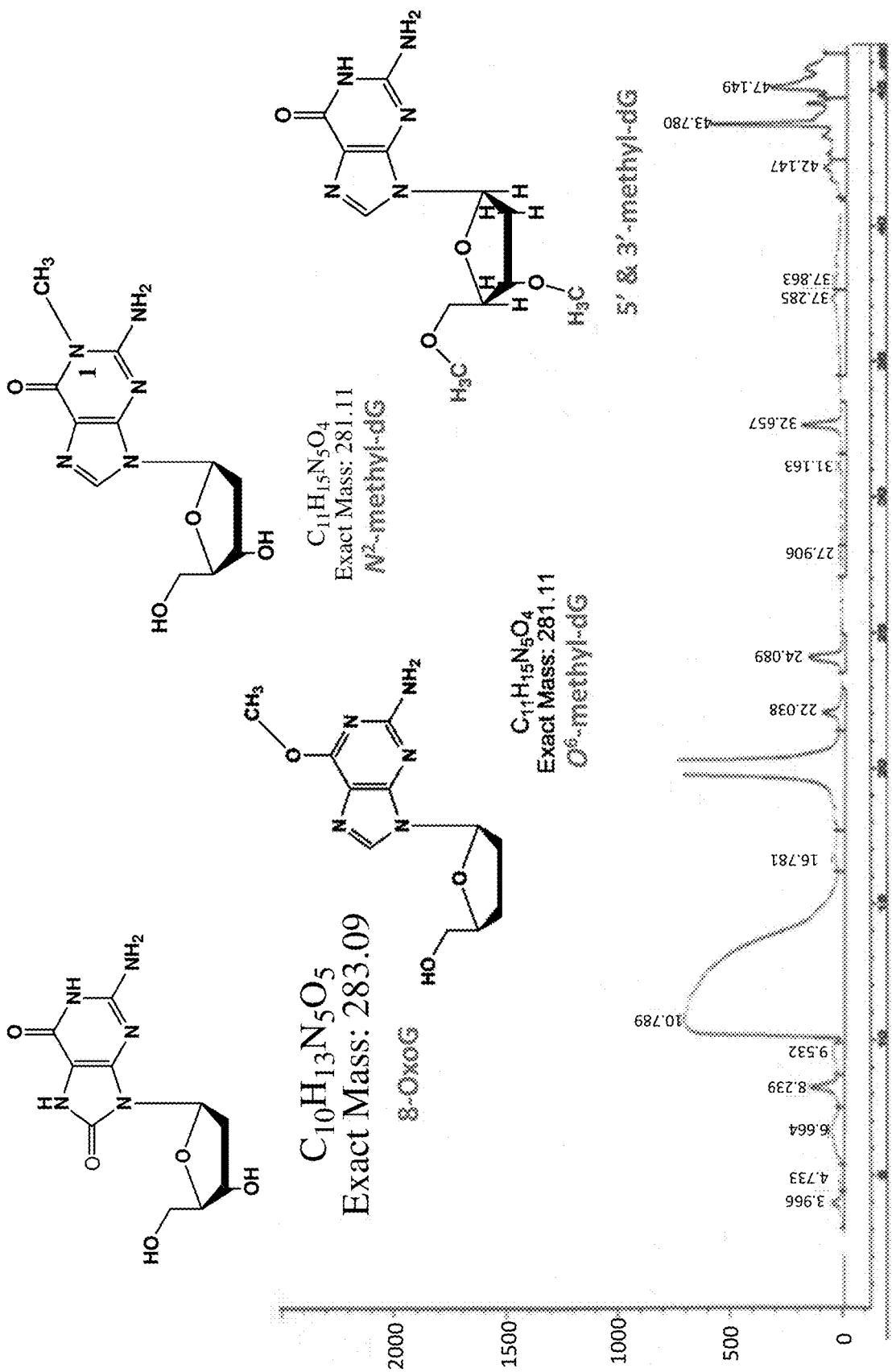
FIG. 8: Other Newly identified NNA-induced dG lesions
Figure 10:
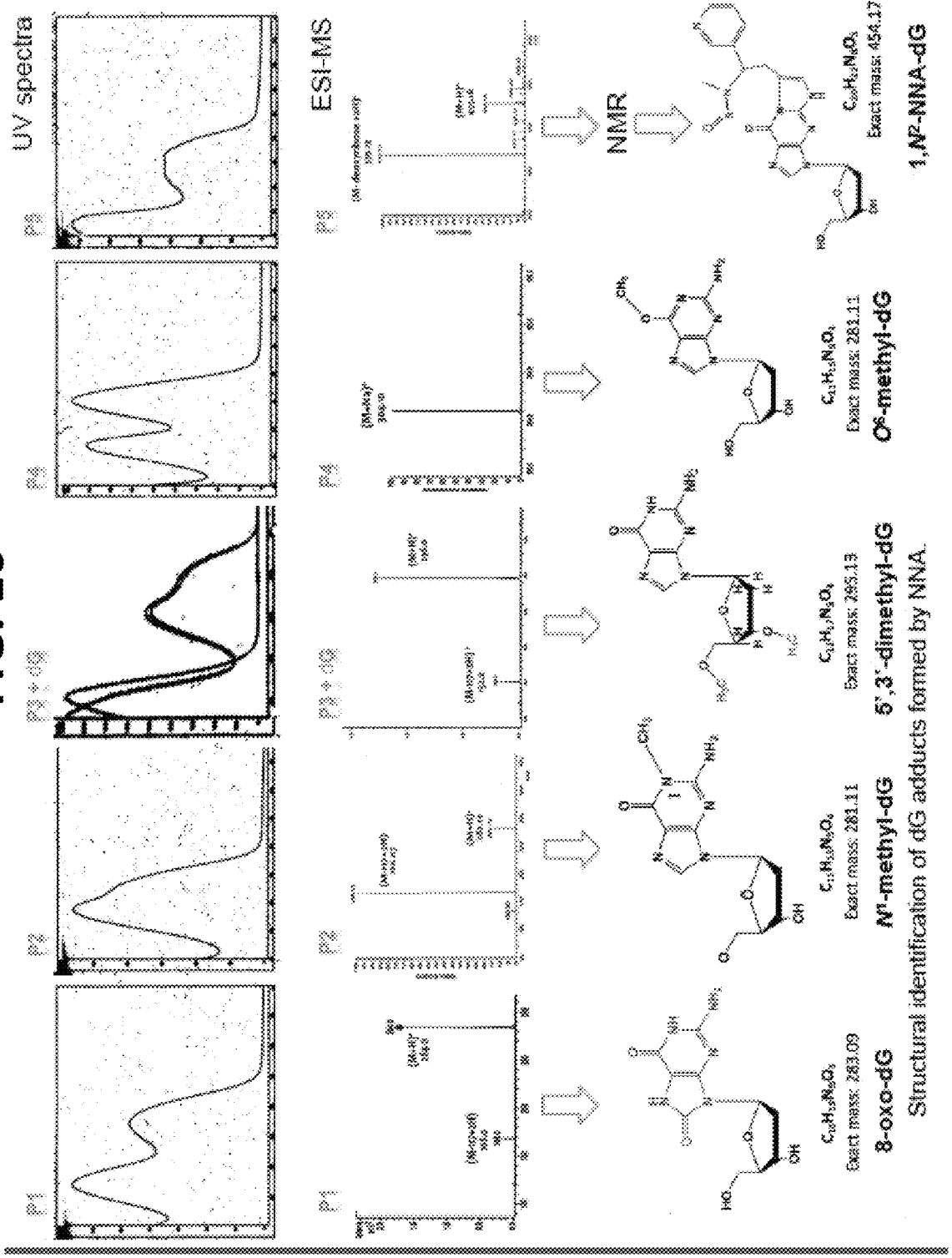
FIG. 10: Structural identification of dG adducts formed by NNA.
Figure 11:
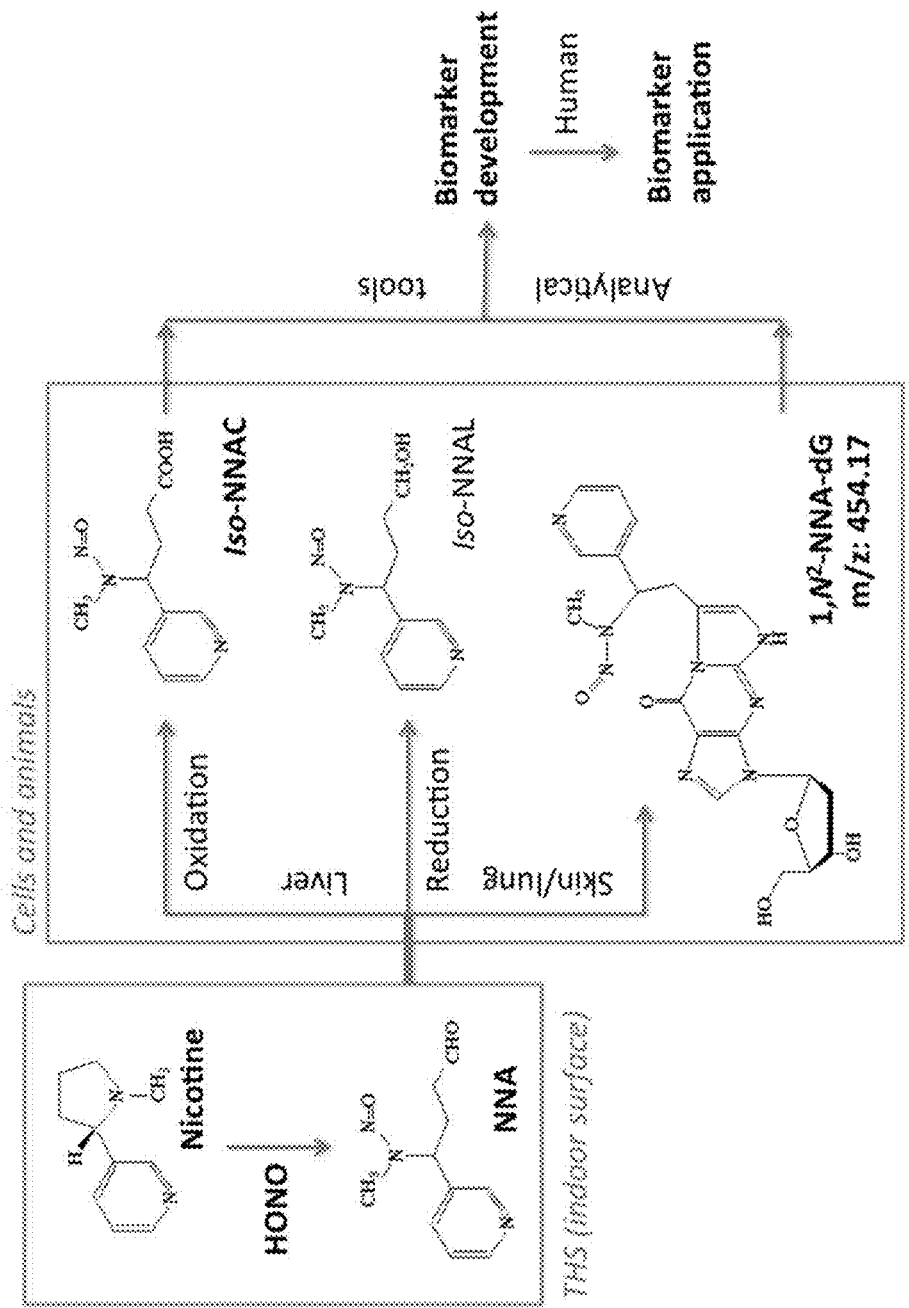
FIG. 11. DNA adduct-forming potency of NNA by identifying five adducts of dG, including a novel exocyclic adduct $1,N^2$-NNA-dG.
Figure 12:
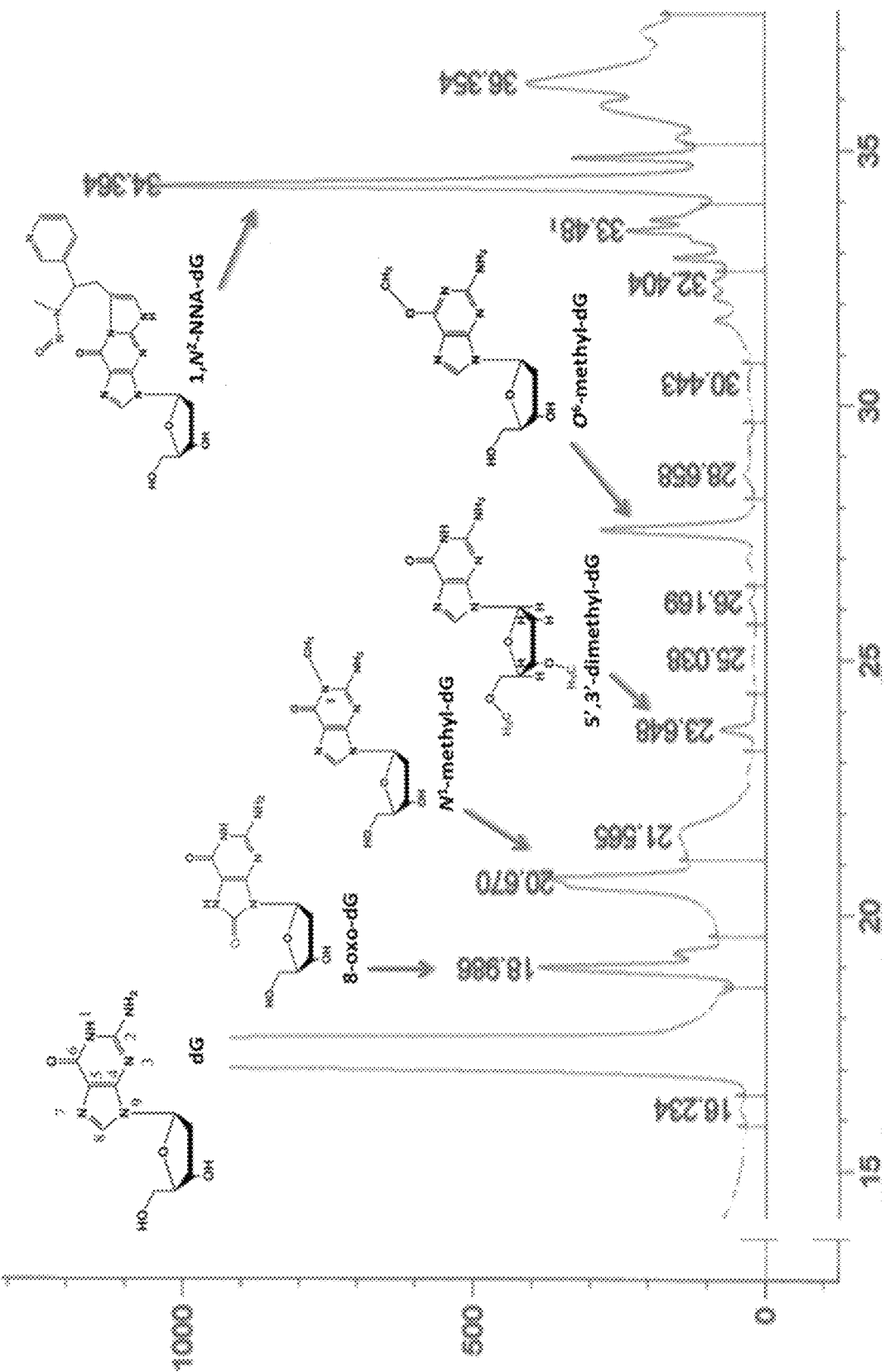
FIG. 12: NNA reaction with dG was separated by reverse phase (C18) chromatography and analyzed by UV spectrum, ESI-MS/MS and 2D-NMR.

Thirdhand smoke (THS) exposure [1] is a newly identified health risk, and one important feature is that it undergoes a chemical transformation during its aging process. An example is the recent indoor chemistry studies, which have revealed that sorbed nicotine reacts with the common indoor pollutant nitrous acid (HONO) to form mutagenic tobacco-specific nitrosamines (TSNAs) (FIG. 3A, right panel) [2]. 1-(N-methyl-N-nitrosamino)-1-(3-pyridinyl)-4-butanal (NNA) is the major TSNA product identified from THS, and is absent in freshly emitted secondhand (SHS) tobacco smoke. Although NNK and NNN are human carcinogens [3] that have been extensively studied, there is little information about the genotoxicity and reactivity of NNA with DNA.

Using the alkaline Comet assay, we examined the potential of NNA to cause DNA strand breaks in cultured human hepatocellular carcinoma (HepG2) cells. Moreover, the ability of NNA to form DNA adducts with dGuo and dCyt in vitro was investigated and characterized using HPLC-UV, electrospray ionization mass spectrometry (ESI-MS/MS) and NMR. The measurement of the above DNA damage can be used to assess the biologically effective dose of exposure, understand the mechanism of the biological impacts of tobacco toxins, and serve as biomarkers of exposure [4]. Our results provide evidence, for the first time, that NNA results in DNA strand breaks in exposed cells [5] and forms multiple DNA adducts in vitro, which may contribute to THS-induced adverse health effects in humans. In addition, the NNA-derived covalent dG adduct identified in this study may be used as a specific biomarker of THS exposure.

A summary of our results show that NNA was identified in THS samples. NNA, similar to NNK, causes significant DNA damage at nM concentrations in human cells as measured using the comet assay. Multiple products are detected and identified from the reaction of NNA with dG in vitro, including the previously characterized adducts 8-oxo-dG, $N^1$-methyl-dG, and $O^6$-methyl-dG. 8-oxo-dG is known to be mutagenic, and is associated with many disease processes. NNA forms an exocyclic dG adduct with a m/z 454.17 in mass spectrum, which has a potential to serve as a biomarker of THS exposure in addition to its biological implications. NNA forms a novel sugar damage, 5',3'-dimethyl-dG. If formed in cells, it would lead to the breakage of the DNA backbone. Lastly, NNA also reacts with dC to form multiple adducts.

These novel findings give insights into the poorly understood cellular mechanisms linking exposure to THS, oxidative stress, DNA damage and cancer risk.

Example 2

Identify and Develop NNA-Derived DNA Adducts as Biomarkers of Exposure and Risk

General Approach: Through collaboration within the Consortium, we will use both cell lines (Talbot) and animal (Martins-Green) systems for NNA- or THS-treatment, followed by identification of specific NNA adducts, particularly 1,$N^2$-NNA-dG, using LC-ESI-MS/MS methods (the "gold standard" for DNA adduct detection) with stable isotope internal standards. Data will be analyzed for: (1) the dose-response relationship; (2) detection limit or practical threshold in relevant cells/tissues; and (3) possible correlation/ratio between the levels of NNA- and NNK-derived specific adducts. We will also compare THS with fresh SHS exposure to examine whether NNA adducts can be useful for their distinction. Finally, we will validate the presence of the NNA adduct(s) in human subjects in lab (Schick) and field studies (Matt). The detection of a specific NNA-DNA adduct(s) provides definitive evidence for THS exposure and its biological effect.

Cell and animal treatments. For cell lines, both HepG2 and BEAS-2B cells (available at LBNL) will be exposed to NNA (Toronto Research Chemicals, TRC) or a THS sample (from Destaillats and Schick) for 24 h at 37° C. at various doses established previously in Hang B, Sarker A H, Havel C, Saha S, Hazra T K, Schick S, Jacob $3^{rd}$ P, Rehan V K, Chenna A, Sharan D, Sleiman M, Destaillats H, and Gundel L A. (2013) Thirdhand smoke causes DNA damage in human cells. *Mutagenesis* 28, 381-91, hereby incorporated by reference. Likewise, human pulmonary fibroblasts (HPF) and embryonic stem cells (from Talbot) will be exposed to explore cell-type specificity of adduct formation.

For mouse experiments, chronic dermal exposure to NNA will be carried out for one month with the dose used in the past, which was shown to cause no side effects. We will use 7 animals per group treated with NNA and vehicle. Both dose-dependent and time course experiments will be performed. At the end of exposure, skin, lung, liver, and blood will be collected for analysis. Depending on the findings of the first experiment, we will vary the dose and time of the exposure as needed. Samples will be provided from skin, liver, lung and blood from THS mice exposed for 6 months and 1 year for analysis (see Martins-Green M, Frankos M, Adhami N, Valdez M, Goodwin B, Lyubovitsky J, Dhall S, Garcia M, Egiebor I, Martinez B, Green H W, Havel C, Yu L, Liles S, Matt G, Destaillats H, Sleiman M, Gundel L A, Benowitz N, Jacob P I, Hovell M F, Winickoff J P, Curras-Collazo M. Cigarette smoke toxins deposited on surfaces: Implications for human health. PLoS ONE. 2014, hereby incorporated by reference). Wounded mouse skin upon exposure to THS will be analyzed for DNA adducts in the skin after injury.

Once a specific NNA-DNA adduct, e.g., $1,N^2$-NNA-dG, is found to be detectable in exposed cells and animals, we will test biosamples (peripheral white blood cells and urine) from the exposed human subjects to THS (Schick) in comparison with controls. As for urine, it is worth trying as some DNA adducts such as etheno adducts are detectable in urine after their enzymatic removal by DNA repair mechanisms.

Preparation of internal standards. Deuterated internal standards for the detection of the corresponding adducts will be prepared according to the previous methods utilized by us for the study of other tobacco carcinogen-derived adducts (Rodriguez B, Yang Y, Guliaev A B, Chenna A, Hang B. Benzene-derived $N^2$-(4-hydroxyphenyl)-deoxyguanosine adduct: UvrABC nuclease incision and its conformation in DNA. *Toxicol Lett.* 2010; 193:26-32; Chenna, A. and Singer, B. (1995) Large scale synthesis of p-benzoquinone-2'-deoxycytidine and pbenzoquinone-2'-deoxyadenosine adducts and their site-specific incorporation into DNA oligonucleotides. *Chem Res Toxicol,* 8, 865-74). As for NNA-DNA standards, we will use 4-[N-(methyl-d3)-N-nitrosamino]-4-(3-pyridyl)butanal (NNA-d3) from TRC. NMR, MS/MS, and UV will be used for structural characterization of the standards. The elucidation of the chemical structure of $1,N^2$-NNA-dG enables the synthesis of the corresponding internal standard.

Detection of NNA-DNA adducts. The whole DNA will be extracted from cultured cells or homogenized animal tissues using the QIAGEN kits. It is now possible to detect DNA adducts using LC-MS/MS and stable isotope internal standards with high sensitivity, accuracy and reproducibility (Singh, R. and Farmer, P. B. (2006) Liquid chromatography-electrospray ionization-mass spectrometry: the future of DNA adduct detection. *Carcinogenesis,* 27, 178-96), in conjunction with off-line purification of adducts with either solid-phase or solvent extraction. To increase the sensitivity of detection, there is a critical requirement for adduct enrichment prior to analysis by LC-MS. This method needs only 10 to 100 μg of DNA and can detect as low as 6 adducts per $10^9$ normal bases (Singh, R. and Farmer, P. B. (2006). *Carcinogenesis,* 27, 178-96). Many types of DNA adducts, including those formed by NNK, NNN, benzo[a]pyrene, and 4-aminobiphenyl, have been detected from tissues of smokers as well as non-smokers exposed to SHS [25]. NNK-derived POB-dG adducts will be used as reference adducts in systems exposed to THS.

Data analysis and potential pitfalls. Dermal exposure with NNA may provide a good chance of detecting adducts because of direct contact. Also Martins-Green found high levels of oxidative DNA damage in wound skin tissues after the mice were exposed to THS chronically. Therefore the skin is a preferred target organ; the respiratory and lung could be the main target organs for inhalation. The lung and liver are well irrigated, and NNA absorbed through the skin would go to these organs first via circulation, therefore they are more likely be exposed to the highest levels of the toxin. In some embodiments, instruments for identification of DNA adducts, in particular high mass resolution Fourier-transform ion cyclotron resonance and Q-Tof quadrupole mass spectrometers that are ideal for identification of DNA adducts. Quantitative analysis with triple quadrupole mass spectrometry systems can be used. Using these methodologies, we expect to detect DNA adducts under the experimental conditions designed, especially in the case of dermal exposure. We expect that only NNA (or THS) through dermal exposure can induce formation of NNA adducts in the skin. Therefore they may serve as route-specific biomarkers of exposure. Although the instrumentation is critical for successful detection of DNA adducts, a considerable challenge would come from the possible low concentrations of chemical compounds such as NNA present in THS. Also, the reactivity of the chemical, DNA repair capacity and persistence of adducts in DNA could all play a role for a better chance of detecting adducts in vivo.

Example 3

Kits to Identify NNA-Derived DNA Adducts as Biomarkers of Exposure and Risk

A specific antibody to detect the NNA-DNA adduct is made, thereby providing methods and compositions for an immunoassay platform test kit that can be used for THS exposure-related environmental health monitoring in human subjects. Human blood will be taken and used for detection, and such a test will be simple, inexpensive, and NNA (thus THS)-specific. Methods of detection may involve using existing technology such as mass spectrometry and imaging, e.g., LC-Mass Spec. The kits may include but are not limited to, instructions, buffers, tubes, vials, lancets or other devices for blood collection, mixing with buffers, and the antibodies in aliquots for detection or attached to substrates.

The immunoassay platform test kit of NNA-DNA adducts are used among people with potential THS exposure, such as babies, children, and housewives who live with smokers, hoteliers and casino workers with occupational exposure, homebuyers and carbuyers living in secondhand houses/cars with previous smoke contamination, and any person with signs and symptoms that are suspected to be associated with exposure to THS.

REFERENCES

1. Matt, G E, Quintana, P J E, Destaillats, H, Gundel, L A, Mohamad, S, Singer, B C, Jacob III, J, Benowitz, N, Winickoff, J P, Rehan, V, Talbot, P, Schick, S, Samet, J, Wang, Y, Hang, B, Martins-Green, M, and Hovell, M F. "Thirdhand tobacco smoke: Emerging evidence and arguments for a multidisciplinary research agenda." *Environ Health Perspect.*, 119: 1218-1226, 2011.
2. Sleiman M, Gundel L A, Pankow J F, Jacob III P, Singer B C, Destaillats H. "Formation of carcinogens indoors by surface-mediated reactions of nicotine with nitrous acid, leading to potential thirdhand smokehazards". *PNAS, USA*, 107: 6576-6581, 2010.
3. Hecht, SS. "Tobacco carcinogens, their biomarkers and tobacco-induced cancer." *Nature Reviews Cancer.* 3: 733-744, 2003.
4. Hang, B. "Formation and Repair of tobacco carcinogen-derived bulky DNA adducts." *J. of Nucleic Acids*, Special issue: DNA Damage, Mutagenesis, and DNA Repair, Editors: Basu, A., Broyde, S., Iwai, S., and Kisker, C, Dec. 20, 2010.
5. Hang, B., Sarker, A. H., Havel, C., Saha, S., Hazra, T. K., Schick, S., Jacob, P. 3rd, Rehan, V. K., Chenna, A., Sharan, D., Sleiman, M., Destaillats, H., and Gundel, L. A. "Thirdhand smoke causes DNA damage in human cells." *Mutagenesis,* 28, 381-391, 2013.
6. Lacoste, S, Castonguay A, Drouin, R. "Formamidopyrimidine adducts are detected using the comet assay in human cells treated with reactive metabolites of 4-(methylnitrosamino)-1-(3-pyridyl)-1-butanone (NNK)." *Mutation Res.,* 600: 138-149, 2006.
7. Hang B, Sarker A H, Havel C, Saha S, Hazra T K, Schick S, Jacob P 3rd, Rehan V K, Chenna A, Sharan D, Sleiman M, Destaillats H, Gundel L A. "Thirdhand smoke causes DNA damage in human cells." *Mutagenesis.* 2013 July; 28(4):381-91. doi: 10.1093/mutage/get013
8. Matt G E, Quintana P J, Destaillats H, Gundel L A, Sleiman M, Singer B C, Jacob P, Benowitz N, Winickoff J P, Rehan V, Talbot P, Schick S, Samet J, Wang Y, Hang B, Martins-Green M, Pankow J F, Hovell M F. "Thirdhand tobacco smoke: emerging evidence and arguments for a multidisciplinary research agenda." *Environ Health Perspect.* 2011 September; 119(9): 1218-26. doi: 10.1289/ehp.1103500. Epub 2011 May 31. Review.
11. Hang B. "Formation and repair of tobacco carcinogen-derived bulky DNA adducts." *J Nucleic Acids.* 2010 Dec. 20; 2010:709521. doi: 10.4061/2010/709521.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

What is claimed is:
1. A method for detection of prior thirdhand smoke (THS) exposure in a sample, comprising the steps of a. obtaining a biological or non-biological sample, wherein said sample is not a biological sample obtained from a firsthand smoker or non-smokers exposed to secondhand smoke (SHS);
b. providing a detector which detects the presence or level of a 2-deoxyguanosine (dG) adduct, and 1-(N-methyl-N-nitrosamino)-1-(3-pyridinyl)-4-butanal (NNA) in a sample; and
c. detecting the presence of said dG adduct, and NNA by the detector above standard baseline levels;

wherein the dG adduct detected having the structure of:

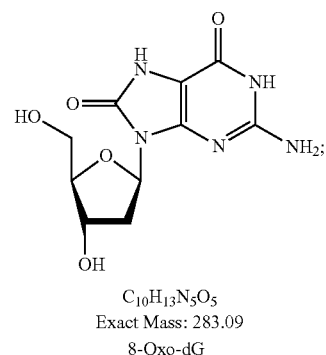

$C_{10}H_{13}N_5O_5$
Exact Mass: 283.09
8-Oxo-dG

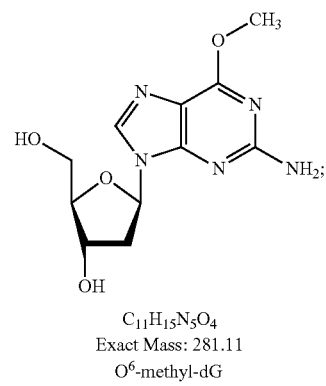

$C_{11}H_{15}N_5O_4$
Exact Mass: 281.11
$O^6$-methyl-dG

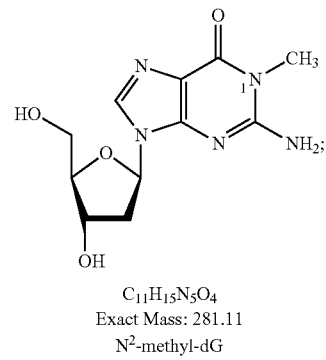

$C_{11}H_{15}N_5O_4$
Exact Mass: 281.11
$N^2$-methyl-dG

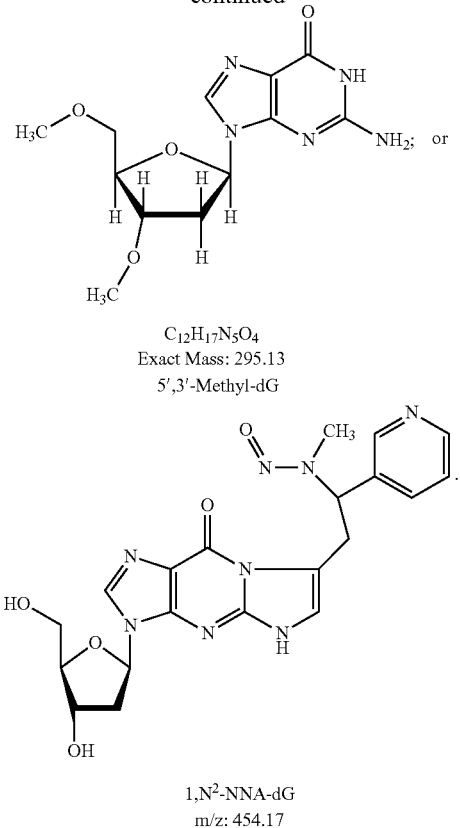

C₁₂H₁₇N₅O₄
Exact Mass: 295.13
5′,3′-Methyl-dG

1,N²-NNA-dG
m/z: 454.17

2. The method of claim 1, wherein the detection of dG adduct presence or level is detected using mass spectrometry or immunohistochemistry.

3. The method of claim 2, wherein the detection is using immunohistochemistry.

4. The method of claim 3, prior to the providing step (a), the method further comprising the step of contacting the sample with an antibody specific for the dG adduct to be detected.

5. The method of claim 1, wherein the sample is a human tissue or bodily fluid.

6. The method of claim 5, wherein the sample is a bodily fluid selected from the group consisting of skin, blood, urine, saliva, and fecal sample.

7. The method of claim 6, wherein the sample is blood.

8. A method for the detection of the presence of DNA damage in a cell as a result of exposure to thirdhand smoke, comprising the steps of:
(a) providing a cell suspected of exposure to thirdhand smoke;
(b) detecting the presence or level of an NNA and a dG adduct of claim 1 in said cell;
(c) determining the level of DNA breaks that the cell has encountered due to thirdhand smoke using NNA and dG adduct-specific probes or compositions to specifically detect NNA and dG adducts as thirdhand smoke biomarkers at the chromosomal location of the DNA break.

9. The method of claim 8, wherein the dG adduct is 8-Oxo-dG; O⁶-methyl-dG; N²-methyl-dG; 5′,3′-Methyl-dG; or 1, N²-NNA-dG.

10. The method of claim 8, wherein the cell is from a human tissue or bodily fluid sample.

11. The method of claim 10, wherein the cell is from a bodily fluid sample and the bodily fluid is selected from the group consisting of blood, urine, saliva, and feces.

12. The method of claim 11, wherein the cell is from a blood sample.

13. The method of claim 1, further comprising step c of initiating an notification signal to indicate the detector has detected the presence and level of a dG adduct or NNA described in step c of claim 1.

* * * * *